(12) United States Patent
Igari et al.

(10) Patent No.: US 7,718,572 B2
(45) Date of Patent: *May 18, 2010

(54) MICROCAPSULE SUSPENSION LIQUID AND PROCESS FOR PRODUCTION THEREOF

(75) Inventors: Yutaka Igari, Fukushima-ken (JP); Tsuneo Okamoto, Fukushima-ken (JP); Yuzi Hori, Fukushima-ken (JP)

(73) Assignee: Kureha Corporation, Tokyo (JP)

( * ) Notice: Subject to any disclaimer, the term of this patent is extended or adjusted under 35 U.S.C. 154(b) by 722 days.

This patent is subject to a terminal disclaimer.

(21) Appl. No.: 10/311,015

(22) PCT Filed: Jun. 11, 2001

(86) PCT No.: PCT/JP01/04900

§ 371 (c)(1), (2), (4) Date: Mar. 12, 2003

(87) PCT Pub. No.: WO01/96009

PCT Pub. Date: Dec. 20, 2001

(65) Prior Publication Data

US 2005/0208144 A1    Sep. 22, 2005

(30) Foreign Application Priority Data

Jun. 12, 2000    (JP)    ............... 2000-175305

(51) Int. Cl.
*A01N 25/28*    (2006.01)
*B01J 13/08*    (2006.01)

(52) U.S. Cl. ............... 504/359; 514/963; 264/4; 427/213.31; 427/213.34; 427/214

(58) Field of Classification Search ............... 504/359; 514/963; 264/4; 427/213.31, 213.34, 214; 424/490

See application file for complete search history.

(56) References Cited

U.S. PATENT DOCUMENTS

| | | | | |
|---|---|---|---|---|
| 4,678,503 A | * | 7/1987 | Barlet et al. | 504/330 |
| 4,900,551 A | | 2/1990 | Ohtsubo et al. | |
| 4,938,797 A | | 7/1990 | Hasslin et al. | |
| 5,252,727 A | * | 10/1993 | Ullmann et al. | 536/123 |
| 5,310,721 A | * | 5/1994 | Lo | 504/359 |
| 5,431,839 A | | 7/1995 | Guillou | |
| 5,716,901 A | * | 2/1998 | Fenderson et al. | 504/134 |
| 5,831,042 A | * | 11/1998 | Knipper et al. | 536/1.11 |
| 5,929,053 A | * | 7/1999 | Murakami et al. | 514/89 |
| 6,486,099 B2 | * | 11/2002 | Igari et al. | 504/359 |

FOREIGN PATENT DOCUMENTS

| | | | |
|---|---|---|---|
| EP | 0 368 576 | | 5/1990 |
| GB | 2073697 | * | 10/1981 |
| GB | 2 187 957 | | 9/1987 |

* cited by examiner

*Primary Examiner*—Jake M. Vu
(74) *Attorney, Agent, or Firm*—Wenderoth, Lind & Ponack, L.L.P.

(57) ABSTRACT

An aqueous microcapsule suspension liquid exhibiting an excellent (long-term) storage stability and allowing easy redispersion and dilution with water even after such a storage, is produced by adding a microorganism-fermented polysaccharide of succinoglycan type as a thickening agent into a microcapsule slurry, or by adding such a microorganism-fermented polysaccharide as a thickening agent to a microcapsule slurry after uniform dilution with water.

1 Claim, 4 Drawing Sheets

MICROCAPSULE SUSPENSION LIQUID AND PROCESS FOR PRODUCTION THEREOF

TECHNICAL FIELD

The present invention relates to a microcapsule suspension liquid which is stable against sedimentation of microcapsules during storage and preservation and capable of easy dilution with water immediately before the use thereof, and a process for production of such a microcapsule suspension liquid.

BACKGROUND ART

Microcapsulation technique is widely adopted for the purpose of, e.g., protection or controlling the rate of liberation to outside of a comminuted core or content material. Examples of the content material include: agricultured chemicals, medicines, toilet materials such as perfume, color-forming materials and adhesive.

Such microcapsules may assume commercial product forms of microcapsules alone or a liquid mixture with a diluting carrier. It is also widely practiced to formulate microcapsules into an aqueous suspension (or emulsion) liquid for spreading the microcapsules to be used after dilution with an appropriate amount of water, as desired, prior to the spreading, e.g., for microcapsules of agricultural chemicals, inclusive of insecticides, fungicides, herbicides, virucides and attractants.

Most important properties for such an aqueous microcapsule suspension liquid include that it is stable without causing sedimentation or separation of the microcapsules during storage and preservation, that even if some sedimentation of microcapsules is caused, the microcapsule suspension liquid or aqueous diluted suspension liquid thereof is capable of easy re-dispersion by a light degree of shaking, and that the microcapsule suspension liquid is easily diluted with water to provide a stable aqueous diluted suspension liquid.

Hitherto, such an aqueous microcapsule suspension liquid has been generally formed by adding materials, such as a thickening agent, a dispersing agent, an anti-freezing agent, an antiseptic agent and a specific gravity-adjusting agent. It has been known that the selection of a thickening agent has a great influence on the suspension stability of the resultant microcapsule suspension liquid. Examples of known thickening agents used for such purpose include: water-soluble synthetic polymers, such as polyethylene oxide, carboxymethylcellulose, and polyvinyl alcohol; water-soluble natural polymers, such as gum arabic, guar gum, locust bean gum, and sodium alginate; (hetero)polysaccharides formed by fomentation with microorganisms, such as xanthan gum, rhamsan gum and welan gum; and natural minerals, such as montmorillonite, and aluminum magnesium silicate. It is also known that polysaccharides formed by fermentation with microorganism as represented by xanthan gum formed by fermentation with a strain of microorganism of the genus *Xanthomonas campestris* particularly exhibit an excellent thickening effect and a relatively stable microcapsule suspension liquid (Japanese Laid-Open Patent Application (JP-A) 2-28813).

However, according to our study, it has been found that a microcapsule suspension liquid formed by using xanthan gum as a thickening agent is relatively stable but still causes some sedimentation or viscosity increase with time and results in a state, such as aggregation or caking, which makes difficult the use thereof by re-dispersion, after long-term of storage.

DISCLOSURE OF INVENTION

Accordingly, a principal object of the present invention is to provide an aqueous microcapsule suspension liquid showing a stabler suspension state.

Another object of the present invention is to provide a process for producing such an aqueous microcapsule suspension liquid showing a stabler suspension state.

According to our study, it has been found that the use as a thickening agent of a microorganism-fermented polysaccharide of succinoglycan type, although it is similarly a microorganism-fermented polysaccharide as the above-mentioned xanthan gum, can provide an aqueous microcapsule suspension liquid, which exhibits a long-term storage stability and a remarkably improved suspension stability even in a so-called mixture-type microcapsule suspension liquid which contains a substance interactive with the content in microcapsules outside the microcapsules and is therefore more liable to lose the suspension stability.

Thus, according to the present invention, a microcapsule suspension liquid comprising: an aqueous medium, and microcapsules comprising a core material and a resinous coating layer coating the core material and suspended in the aqueous medium in the presence of a thickening agent, wherein the thickening agent is a microorganism-fermented polysaccharide of succinoglycan type.

We have also found it possible to provide a stabler aqueous microcapsule suspension liquid by using a microorganism-fermented polysaccharide inclusive of the succinoglycan type and the xanthan gum type as a thickening agent and improving a state of mixture of the thickening agent and the microcapsules.

More specifically, according to another aspect of the present invention, there is provided a process for producing a microcapsule suspension liquid, comprising:

(I) a step of mixing a thickening agent comprising a microorganism fermented polysaccharide for dilution with water to form a dilute thickening agent aqueous solution, and (II) a step of mixing a microcapsule suspension liquid comprising an aqueous medium and microcapsules comprising a core material and a resinous coating in the aqueous medium with the above-formed dilute thickening agent aqueous solution.

DESCRIPTION OF THE PREFERRED EMBODIMENTS

Figure 1:
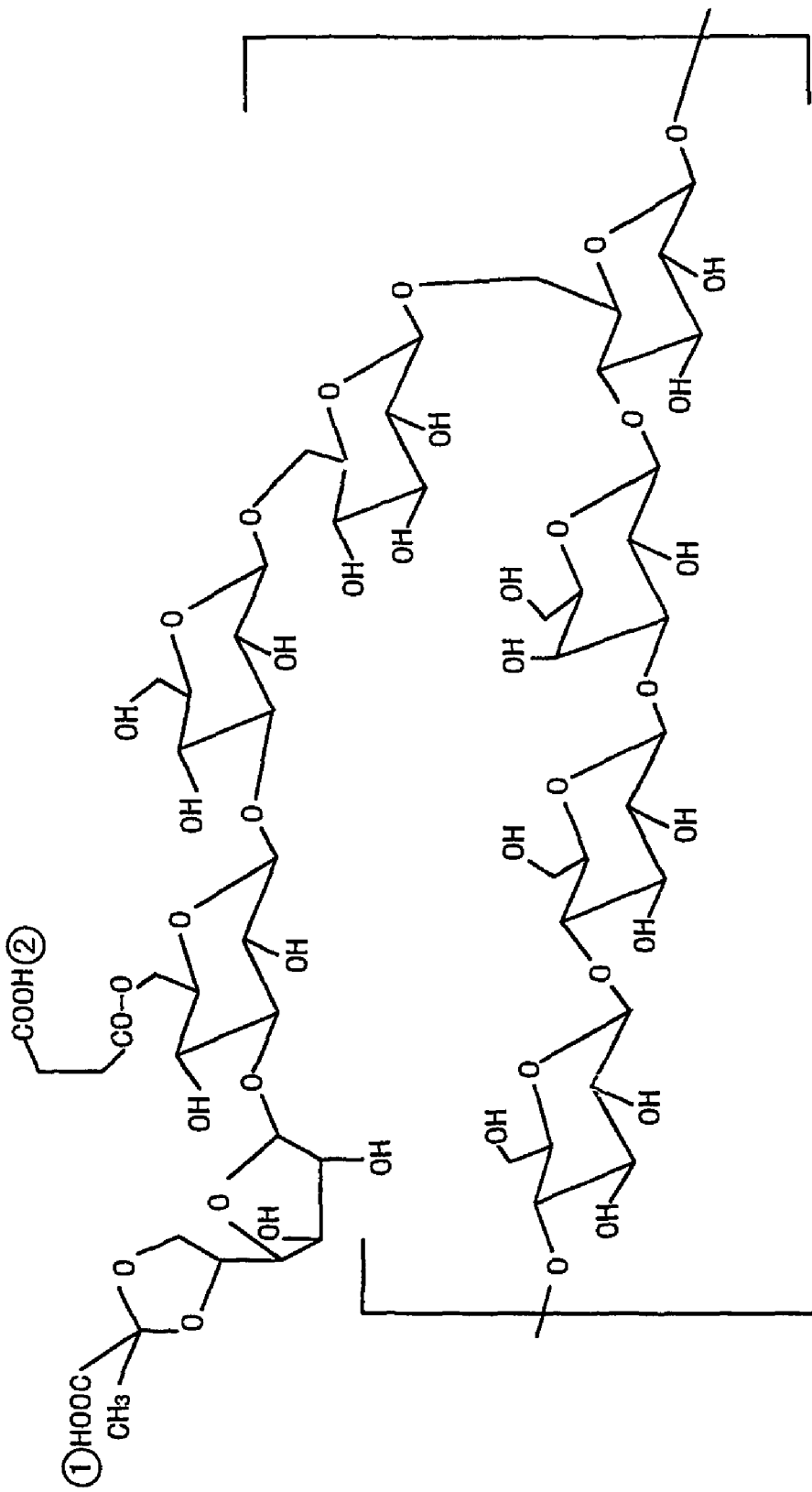
FIG. 1 shows a structural formula of a commercially available succinoglycan polysaccharide.

The microcapsule suspension liquid according to the present invention comprises microcapsules comprising a core material and a resinous coating layer coating the core material and suspended in an aqueous medium in the presence of a thickening agent.

(Microcapsule)

The core material can basically be any material but may preferably comprise a liquid or solid hydrophobic substance. Such a core material may generally be formed into microcapsules in a slurry form through a microencapsulation process including a physical, physicochemical or chemical film forming step in an aqueous medium, in most cases. Preferred examples of microcapsules may include: (a) a microcapsule having a resinous coating layer comprising a polycondensate of a water-soluble cationic resin, an anionic surfactant and an amino resin prepolymer (as disclosed in U.K. Laid-Open Patent Application (GB-A) 2113170), (b) a microcapsule having a resinous coating layer comprising a polycondensate of a water-insoluble monomer, and (c) a microcapsule having a resinous coating layer comprising a successive laminate including a solidified layer of coacervate of a water-soluble cationic amino resin and an anionic surfactant and a layer of polycondensate of amino resin prepolymer (as disclosed in International Application PCT/JP01/0055), respectively, coating a hydrophobic core material. As an example of the microcapsule (b), a microcapsule may be formed by an interfacial polymerization process comprising dispersing droplets of a hydrophobic solution comprising a polyisocyanate and a core material in an aqueous solution containing a polyhydric alcohol and a water-soluble polymer as a suspension and dispersion aid, followed by film formation in a temperature range of generally 5-80° C., preferably 40-80° C. for 0.5-48 hours, preferably 12-48 hours. Among the above, the microcapsules (a) and (c) may be classified as microencapsulation products according to the in-situ polymerization process, and the microcapsule (b) may be classified as a microencapsulation product according to the interfacial polymerization process. The present invention is applicable to both types of microcapsules but may rather preferably be applicable to the formation of a stable aqueous suspension liquid of microcapsules obtained through the in-situ polymerization process, of which the microcapsule suspension stability is liable to be lost.

As a preferred class of examples of hydrophobic material constituting the core material, agricultural chemicals including insecticides, fungicides, herbicides, virucides (biotic agricultural chemicals), attractants, repellents, plant growth regulators and rodenticides, are enumerated. Other examples of the hydrophobic material suitable for microencapsulation may include lubricants, inorganic materials, color formers, catalysts, adhesives, perfume and medicines. These hydrophobic materials may be either solid or liquid. Specific examples of hydrophobic materials suitable for microencapsulation may include: as agricultural chemicals, insecticides, such as chlorpyrifos, ethoprophos, NAC (carbaryl), BPPS (propargite), MEP (fenitrothion), diazinon, DDVP (dichlorvos), propaphos, disulfoton, CVP (chlorfenvinphos), CVMP (tetrachlorvinphos), CYAP (cyanophos), isoxathion, pyridaphenthion, chlorpyrifos-methyl, malathion, PAP (phenthoate), DMTP (methidathion), sulprofos, pyraclofos, DEP (trichlorfon), EPN, MIPC (isoprocarb), BPMC (fenobucarb), PHC (propoxy), XMC, carbosulfan, benfuracarb, furathiocarb, fenpropathrin, fenvalerate, cycloprothrin, ethofenprox, silafluofen, bensultap, imidacloprid, acetamiprid, buprofezin, endosulfan, fipronil, chlorfenapyr, DCIP, fosthiazate, natural pyrethrins, and synthetic pyrthrins, such as allethrin and tralomethrin; fungicides, such as probenazole, isoprothiolane, IBP (iprobenfos), EDDP (edifenphos), iminoctadine albesilate, TPN (chlorothalonil), dichlo-fluanid, TBZ (thiabendazole), oxine-copper, zineb, maneb, mancozeb, thiram, tolclofos-methyl, phthalate, pyroquilon, carpropamid, thiophanate-methyl, iprodione, benomyl, procymidone, mepronil, flutolanil, triflumizole, prochloraz, azoxystrobin, kresoxim-methyl, metominostrobin, dazomet, diclomezine, pencycuron, and dithianon; herbicides, such as, butachlor, oxadiazon, bentazone, DBN (dichlobenil), pyributicarb, ACN (quinoclamine), clomeprop, naproanilide, cyhalofop-butyl, quizalofop-ethyl, phenmedipham, thiobencarb, orbencarb, molinate, thenylchlor, bromobutide, mefenacet, cafenstrole, asulam, pyrazosulfuron-ethyl, imazosulfuron, atrazine, ametryn, PAC (chloridazon), bentazone, pyrazolynate, pyrazoxyfen, benzofenap, trifluralin, benfluralin, pendimethalin, piperophos, butamifos, glyphosate-isopropylammonium, glufosinate-ammonium, DCBN (chlorthiamid), and sethoxydim; biotic agricultural chemicals, such as BT (Bacillus thuringiensis Berliner); attractants, such as codlelure, surflure, smalure and phycilure; plant growth regulators, such as forchlorfenuron, uniconazole, and piperonyl butoxide; rodenticides, such as coumatetralyl and chlorophacinone; and repellents.

The above-mentioned names of effective components of agricultural chemicals are general names listed in "Agricultural Chemical (Nohyaku) Handbook 1998-edition" published from Nippon Shokubutsu Boeki Kyokai, Japan.

Examples of hydrophobic core materials other than agricultural chemicals may include: lubricants, such as gear oil, machine oil, silicone oil, wax and liquid paraffin; inorganic materials, such as titanium oxide, barium titanate, and toner (magnetic powder); fluorine-containing resins, such as PTFE (polytetra-fluoroethylene); color formers, such as leuco dyes, dyes, pigments and printing inks; detector agents, such as paradium compounds (leaked hydrogen detector) and bromine compounds (ammonium detector); and catalysts including vulcanization promoters, such as PX (zinc N-ethyl-N-phenyldithiocarbamate) added to rubber and anti-weathering agents, such as PA (1-(N-phenylamino)-naphthalene) and AD (dialkyldiphenyl-amine) (added, e.g., to tires, particularly two-layered tires and shoe-sole rubber; additives (plasticizers) to plastics and rubbers, such as DEP (diethylphthalate), BPO (benzoyl peroxide), DBF (dibutyl fumarate), DBS (dibutyl sebacate), thiokol TP; blowing agents (volatile organic solvents), perfume, and medicines.

These hydrophobic materials may ordinarily be microencapsulated for respective species individually, but can be microencapsulated in two or more species together if they are chemically stable in the co-presence. Further, in the case where the hydrophobic core material is liquid, it can be dissolved in a water-insoluble solvent, such as xylene, toluene, kerosene or vegetable oil, for the purpose of alleviating the odor, toxicity, volatility, etc. In the case where the hydrophobic core material is solid, the core material can be microencapsulated as it is, or after being melted by heating to a temperature above its melting point, or after being dissolved in a water-insoluble solvent, such as xylene, toluene or kerosene. A solid hydrophobic material can also be finely pulverized and dispersed together with a surfactant as a dispersing agent, before microencapsulation thereof. The dispersing agent may comprise a known surfactant, preferred examples of which may include: anionic surfactants, such as aliphatic acid salts, higher alcohol sulfuric acid salts, alkylbenzenesulfonic acid salts, alkyl-naphthalenesulfonic acid salts; condensates of formalin with naphthalenesulfonic acid, alkylnaphthalenesulfonic acids or other aromatic sulfonic acids; sulfosuccinic acid salts, alkylarylsulfonic acid salts and alkylphosphate salts. At the time of dispersion or pulverization of a hydrophobic core material, it is also possible to add a thickening agent, such as a water-soluble polymer.

According to a first embodiment of the present invention, a mass of microcapsules as described above are dispersed in an aqueous medium in the presence of a thickening agent comprising a microorganism-fermented polysaccharide of succinoglycan type to obtain a microcapsule suspension liquid according to the present invention. This is generally performed by adding, into a microcapsule slurry obtained through a process as described above, the thickening agent together with diluent water, and further optional dispersion aids, such as a dispersing agent comprising a surfactant, an anti-freezing agent containing glycol as a component, or an anti-foaming agent containing silicone as a component.

The microorganism-fermented polysaccharide of succinoglycan type per se used as a thickening agent in the present invention is disclosed in U.S. Pat. No. 5,252,727 (corr. to Japanese Patent Publication (JP-B) 7-42323) as a heteropolysaccharide produced by fermentation of a medium comprising a source of assimilable carbon (such as glucose, saccharose or hydrolysis products of starch), by a strain of *Agrobacterium tumefaciens* I-736 or mutant or recombinant thereof, and characterized by an intrinsic viscosity of 30-250 dl/g (corr. to a molecular weight of ca. $6 \times 10^6$-$10 \times 10^6$) and containing recurring units of glucose, galactose and pyruvic, succinic and acetic acids or, salts thereof, in the respective molar ratios of 5-8/1-2/0.5-2/0.5-2/0.05-2. A commercially available example thereof is "RHEOZAN" (made by Rhone-Poulene Agrochimie and imported into Japan by Rhodia Nikka K.K.), which was also used in the present invention. According to the technical brochure for the same "RHEOZAN", the polysaccharide is represented by a structural formula shown in FIG. 1 and, in view of a measured pH of 7-9 at a concentration of 2 g/liter, it is understood that COOH(1) in the pyruvic acid unit and COOH(2) in the succinic acid unit are at least partially converted in salts with Na, K, Ca, etc., and a small portion of $CH_2OH$ groups in the glucose (or galactose) units are acetylated. The heteropolysaccharide of succinoglycan type is also used in U.S. Pat. No. 5,431,839 (corr. to JP-A 7-69609).

Figure 2:
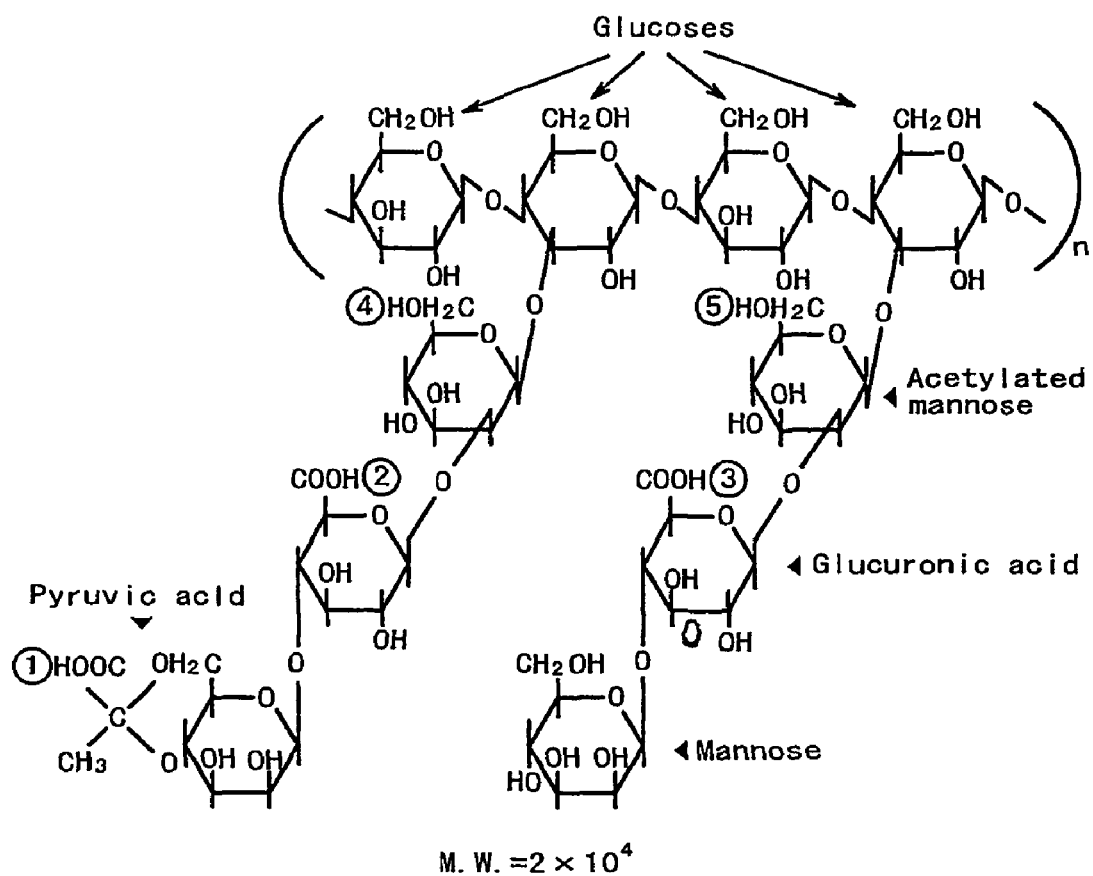
FIG. 2 shows a structural formula of a commercially available xanthan gum.

In contrast thereto, xanthan gum which has been conventionally used for providing an aqueous microcapsule suspension liquid is a gum (heteropolysaccharide) produced by fermentation with a strain of *Xanthomonas campestrics*. Commercially available examples thereof include: "KELZAN" available from Kelco Division of Merck & Co. Inc., and "RHODOPOL" available from Rhone-Poulene Chimie, which are both disclosed to contain recurring units of glucose/mannose/glucuronic acid/pyruvic acid in the respective molar ratios of about 2/2/1/–0.5. The technical brochure for "RHODOPOL" shows a structural formula as shown in FIG. 2 wherein COOH(1) in the pyruvic acid unit and COOH(2) and COOH(3) in the glucuronic acid units are expressed in forms of salts with Na, etc., and $CH_2OH(4)$ and $CH_2OH(5)$ in the mannose unit are expressed in an acetylated form. The molecular weight is said to be ca. $2 \times 10^6$. A measured pH was 6-8 at a concentration of 10 g/liter, which was similar to that of the above-mentioned heteropolysaccharide of succinoglycan type used in the present invention (hereinafter sometimes also referred to as "succinoglycan gum").

Comparing the xanthan gum and the succinoglycan gum, both are classified as microorganism-fermented polysaccharides and also as water-soluble natural polymers. Further, Comparing FIGS. 1 and 2, both commonly have main chains comprising β-1,4-glucose bond chains. Accordingly, the specifically better suspension stabilizing effect of the succinoglycan gum used in the present invention over the xanthan gum may reasonably be attributable to an overall effect in an aqueous solution thereof of factors, such as a relatively large molecular weight, longer side chains, the presence of succinic acid units in the side chains and the presence of galactose units instead of mannose units.

In the microcapsule suspension liquid according to the present invention, the thickening agent represented by the succinoglycan gum may preferably be used in a proportion of 0.1-10 wt. parts, particularly 0.2-5 wt. parts, per 100 wt. parts of microcapsules. Below 0.1 wt. part, the suspension liquid stabilization effect by the addition thereof is scarce, and in excess of 10 wt. parts, the product suspension liquid is caused to have a high viscosity so that the production thereof becomes difficult, and the operation for dilution thereof is liable to be difficult. The succinoglycan gum used in the present invention can be used in combination with other thickening agents inclusive of other water-soluble thickening agents, such as xanthan gum, polyvinyl alcohol, carboxymethyl cellulose and chitosan, or other types of thickening agents, such as powder minerals of montmorillonite and bentonite, and alumina sol, within an extent of not adversely affecting the specific thickening and suspension-stabilizing effects of the succinoglycan gum. In this instance, the total amount of the thickening agents used in combination should be in the above-mentioned range.

In addition to the thickening agent as represented by the succinoglycan gum, it is also possible to add known dispersion aids, as desired. Examples of such dispersion aids may include: additives for facilitating dilution with water, generally called a dispersing agent, such as surfactants inclusive of anionic surfactants, such as carboxylic acid salts, sulfuric acid ester salts, sulfonic acid salts, and phosphoric acid ester salts, and nonionic surfactants, such as those of polyethylene glycol type and polyhydric alcohol type, or water-soluble polymers, such as sodium polyacrylate, used in an amount of 0.2-30 wt. parts, preferably 0.5-20 wt. parts, per 100 wt. parts of the microcapsules; anti-freezing agents, e.g., for preventing freezing at −5° C., in consideration of use in a cold weather region, comprising water-soluble glycols, such as propylene glycol, ethylene glycol and diethylene glycol, used in an amount of 10-30 wt. parts per 100 wt. parts of the microcapsules; anti-foaming agents for facilitating the production or dilution with water of microcapsule suspension liquid and spreading or sprinkling of the (diluted) microcapsule suspension liquid while preventing the foaming of the liquid, such as silicone oils, octyl alcohol and alkylene glycols, preferably silicone oils, used in an amount of 0.01-0.25 wt. part per 100 wt. parts of the microcapsules; and further antiseptic agents for preventing the occurrence of fungi, such as sodium benzoate, potassium sorbate, parahydroxy benzoate and salicylic acid derivative, specific gravity-adjusting agents such as sodium sulfate and urea, and protecting agents.

In the microcapsule suspension liquid thus produced, the core material may ordinarily occupy 0.1-40 wt. %, preferably 5-30 wt. %, of the total suspension liquid.

According to a second embodiment of the present invention, a microcapsule suspension liquid is produced through a process comprising (I) a step of mixing a thickening agent comprising a microorganism-fermented polysaccharide for dilution with water to form a dilute thickening agent aqueous solution, and (II) a step of mixing a microcapsule suspension liquid comprising an aqueous medium and microcapsules comprising a core material and a resinous coating in the aqueous medium with the above-formed dilute thickening agent aqueous solution.

According to our study, a known thickening agent comprising a conventional microorganism-fermented polysaccharide hitherto used for preparing a microcapsule suspension liquid, such as xanthan gum, exhibits an excellent thickening effect but cannot obviate separation and aggregation of microcapsules after a long term of storage of the microcapsule suspension liquids after a long term of storage of the microcapsule suspension liquid. A reason therefor has been found to be because, from an extremely microscopic viewpoint, the thickening agent is not uniformly dispersed in the microcapsule suspension liquid. Particularly, such a thickening agent has been generally added together with other dispersion aids, such as a so-called dispersing agent, an anti-freezing agent and an anti-foaming agent, to and mixed with a microcapsule slurry produced through a microencapsulation step. It has been however formed that such a mixing step is not necessarily completely effective for microscopically uniform dispersion of such a thickening agent comprising a microorganism-fermented polysaccharide, so that the thickening and suspension liquid-stabilizing effect of the thickening agent has not been fully exhibited. As a result of further study, it has been found possible to provide a microcapsule suspension liquid exhibiting a remarkably improved long-term storage stability by once separately dispersing the thickening agent in water to form a dilute thickening agent dispersion or solution and then mixing the dilute thickening agent dispersion or solution with a microcapsule slurry separately formed. This effect can also be attained as an effect of further stabilizing the microcapsule suspension liquid even in the case of using the succinoglycan gum as the thickening agent.

As a more preferred embodiment, in the step (I), it is preferred to first disperse and dilute the thickening agent comprising a microorganism-fermented polysaccharide as represented by the succinoglycan gum and the xanthan gum together with a water-miscible solvent to form a mixture and then mix the mixture with water by means of a high-speed mixing machine to form a dilute thickening agent dispersion liquid. The water-miscible solvent may preferably be a substantially non-volatile (i.e., non-volatile or only scarcely volatile) solvent, specific examples of which may include: monohydric alcohols, such as ethanol, isopropanol and 1-butanol; polyhydric alcohols, such as ethylene glycol and propylene glycol, and derivatives thereof; and nitrogen-containing heterocyclic compounds, such as N-methylpyrrolidone and N-alkylpyrrolidones. It is further preferred to use as the water-missible solvent a glycol, such as polypylene glycol, ethylene glycol or diethylene glycol, which is preferably added as an anti-freezing agent in a microcapsule suspension liquid to be used outdoors, such as that of microcapsules containing an agricultural chemical. The water-miscible solvent may generally be used in a proportion of 1-80 wt. parts, preferably ca. 10-60 wt. parts, per 1 wt. part of the thickening agent. Further, it is also possible to add a hardly water-soluble substance, such as vegetable oil or mineral oil in a proportion of ca. 1-10 wt. parts, for example, for improving the dispersibility of the thickening agent. In the aqueous dilute thickening agent dispersion liquid or solution obtained through the step (I), the thickening agent may preferably be contained in a concentration of ca. 0.1-5 wt. %, in view of the processability.

Then, in the step (II), the aqueous dilution liquid of thickening agent obtained above is mixed with a microcapsule slurry prepared in a separate microencapsulation step to obtain a microcapsule suspension liquid. Simultaneously with or, more preferably, after mixing of the dilution liquid and the slurry, the above-mentioned other dispersion aids, inclusive of a dispersing agent comprising a surfactant, and an anti-forming agent such as silicone oil, may preferably be added to provide the product microcapsule suspension liquid with properties adapted to an intended use thereof.

In other words, in a preferred mode according to the second embodiment of the present invention, a water-miscible organic solvent such as a glycol which has been optionally used, e.g., as an anti-freezing agent together with other dispersion aids, is selectively mixed with a thickening agent for preparation of an aqueous dilution liquid of the thickening agent, thereby improving the microscopic dispersion of the thickening agent comprising a microorganism-fermented polysaccharide in a microcapsule suspension liquid to be obtained by further mixing thereof with a microcapsule slurry and causing the thickening agent to exhibit its microcapsule suspension liquid-stabilizing effect to the maximum, to allow the production of a microcapsule suspension liquid capable of long-term storage.

Figure 3:
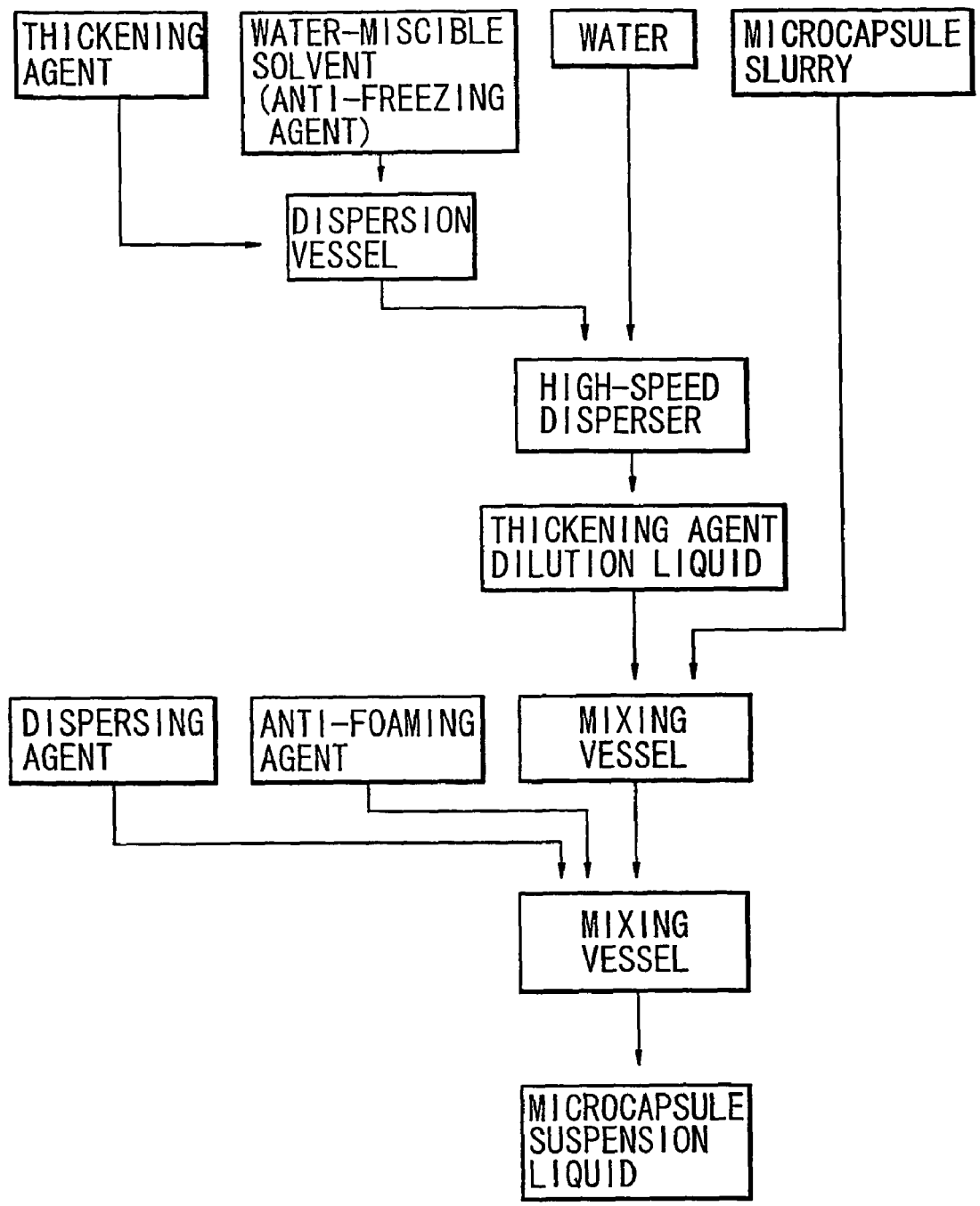
FIG. 3 is a flow chat of an embodiment of the process for producing a microcapsule suspension liquid according to the invention.

The above-mentioned preferred mode of the process for producing a microcapsule suspension liquid according to the present invention is summarized in FIG. 3.

The excellent storage stability of the microcapsule suspension liquid is particularly effectively utilized in the case of so-called "mixture use" (i.e., an embodiment of microcapsule suspension liquid containing two or more effective components in the microcapsule suspension liquid). One of the effective components is contained in a type of microcapsule, and the other effective component can be contained in another type of microcapsule wherein the stability of the resultant microcapsule suspension liquid containing two types of microcapsules is not substantially different from that of a microcapsule suspension liquid containing a single type of microcapsule. The present invention is particularly preferably used in a preferred mode of "mixture use" wherein the other effective component is directly dispersed or dissolved in the aqueous dispersion medium constituting the microcapsule suspension liquid and also containing the microcapsules enclosing the one effective component. Such a "mixture use" of microcapsule suspension liquid is generally adopted for having the microcapsule suspension liquid contain a substance interacting with a core material enclosed within a microcapsule. Example of the interaction may include: compensation, e.g., by inclusion of a rapidly acting substance in combination with an encapsulated core material to be gradually liberated to exhibit a slow activity; multiplication of functions, e.g., by inclusion of an herbicide in combination with an insecticide of core material, by inclusion of a germicide in combination with an insecticide of core material, and by inclusion of a germicide in combination with a herbicide of core material; and promotion or suppression of an activity of the liberated core material as by inclusion of a promoter or a retarder. The inclusion of such an interacting substance is generally preferable for the purpose of compensation, multiplication and modification (promotion or suppression) of function of the microcapsule suspension liquid principally given by the core material but, on the other hand, rather adversely affects the suspension stability of the microcapsule suspension liquid unlike the addition of a dispersion aid functioning to stabilize the microcapsule suspension liquid.

However, as the microcapsule suspension liquid according to the present invention is provided with a remarkably improved suspension stability compared with conventional microcapsule suspension liquids, the stability of suspension thereof can be retained at a high level even in the case of the mixture use. This effect is particularly effectively attained in the case of combination of the first and second embodiments of the present invention (i.e., in the case of using the succinoglycan gum as a thickening agent in the second embodiment of the present invention).

EXAMPLES

Hereinbelow, the present invention will be described more specifically based on Examples and Comparative Examples, wherein "%" for expressing a composition is used to mean "wt. %" unless otherwise noted specifically.

First of all, some Production Examples for preparation of microcapsule slurries prior to production of microcapsule suspension liquids, will be described.

Production Example 1

Production of Microcapsule (c)

Figure 4:
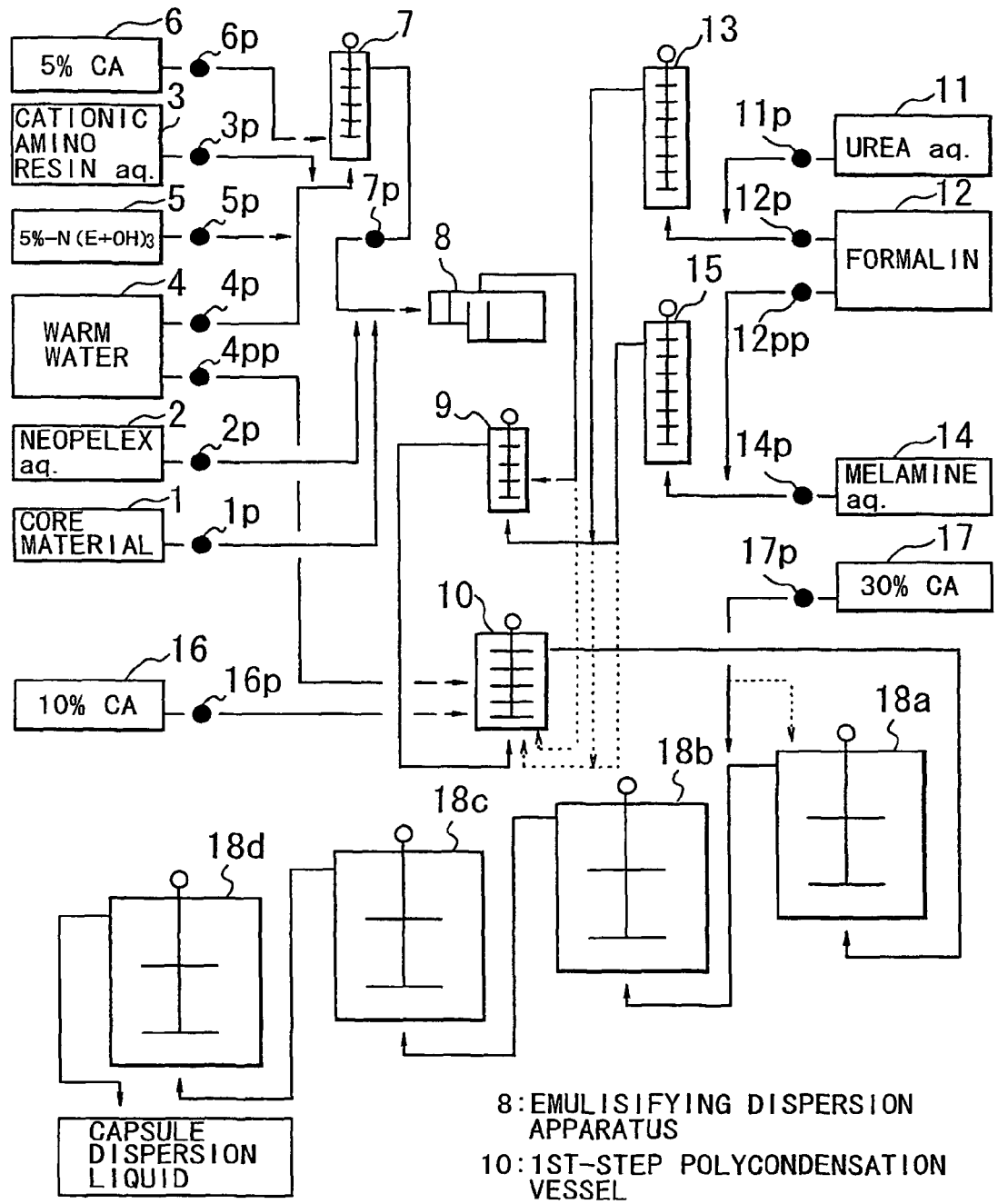
FIG. 4 is a flow chart of an example of process for producing microcapsule slurry.

A microcapsule slurry was prepared in the same manner as in Example 1 of PCT/JP01/0055 by using an apparatus system as substantially shown in FIG. 4.

(First Coating Step)

A core material (1) of chlorpyrifos (an insecticide, liquid at 45° C., available under a trade name of "LENTREK" from Dow Chemical Co.) and an anionic surfactant (2) of 1% aqueous solution of sodium dodecylbenzenesulfonate ("NEOPELEX" available from Kao K.K.) were provided so as to be supplied at rates of 78 kg/h and 9.0 kg/h, respectively.

Separately, warm water (at 50° C.) (4) at 110 kg/h, cationic urea resin (3) ("U-RAMIN P-1500", in the form of an aqueous solution (solid content=ca. 40 wt. %), available from Mitsui Kagaku K.K.) at 7.9 kg/h and a 5%-aqueous solution of triethanolamine (N(EtOH)$_3$) (5) at 6.5 kg/h were supplied to an emulsion mother liquid mixing vessel (7) and mixed with each other therein, and then the pH of the mixture was adjusted to 4.75 by adding a 5%-citric acid (CA) aqueous solution (6) as an acid catalyst. The thus pH-adjusted mixture liquid at 50° C. was continuously supplied together with the above-mentioned core material (1) and anionic surfactant aqueous solution (2) to an emulsifying dispersion apparatus (8) (having an inner volume of ca. 0.5 liter and providing a residence time of 7-10 sec., "TK-HI-Line Mill HL-50 type", available from Tokushu Kika Kogyo K.K.) wherein the dispersion conditions were set to provide a liquid droplet average-particle size of 3-5 μm at 45° C., thereby obtaining a dispersion liquid containing coacervate-coated core material particles.

(2) Preparation of Amino Resin Prepolymer

A 30%-urea aqueous solution (11) at 15.2 kg/h and formalin (37%-formaldehyde aqueous solution adjusted to pH 8.0 by addition of 20%-triethanolamine aqueous solution) (2) at 11.1 kg/h were supplied to a resin prepolymer reaction vessel (13), and were caused to reside therein for 70 min. at 70° C. under stirring to continuously produce a urea resin prepolymer (formaldehyde/urea=1.8 (by mol)) liquid.

Separately, a 18%-melamine aqueous dilution liquid at 32.9 kg/h and formalin (adjusted to ph 8.0 by addition of 20%-triethanolamine aqueous solution) (12) at 19.1 kg/h were supplied to a resin prepolymer reaction vessel (15) and were caused to reside therein for 35 min. at 50° C. under stirring to continuously produce a melamine resin prepolymer (formaldehyde/melamine=4 (by mol)) liquid.

(3) Second Coating Step (Microencapsulation)

The dispersion liquid prepared in the step (1) mentioned above and the resin prepolymer liquids (13 and 15) prepared in the step (2) above were continuously and uniformly mixed each other in a mixing vessel (9), and the resultant mixture liquid was introduced into a first-step polycondensation vessel (10), to which an acid catalyst of 10%-citric acid aqueous solution was added so as to continuously adjust the pH at 4.75. After residence for ca. 10 min. therein, warm water (4) was continuously added thereto at a rate of 50 kg/h, and the system was held at 50° C. under stirring for a residence time of 30 min. Then, the effluent liquid from the vessel (10) was then supplied to a first second-step polycondensation vessel (18a) for 5 hours of stirring at 50° C. therein, followed by 5 hours of stirring at 50° C. in a second vessel (18b) while adding an acid catalyst of 30%-citric acid aqueous solution (17) at a rate of 3 kg/h so as to continuously adjust the pH to 2.8, and further 5 hours each of stirring at 50° C. in third and fourth vessels (18c and 18d) to complete the microencapsulation, thereby obtaining, a slurry of microcapsules having a volume-average particle size (Dv) of 4.5 μm.

Production Example 2

Microencapsulation was performed substantially in a similar manner as in Production Example 1 except for the following modifications.

The first coating step was repeated except for changing the core material (1) to 60 kg/h of ethoprophos in an undiluted form ("MOCAP", an insecticide available from Rhone-Poulenc Agrochimie), and supplying 118.0 kg/h of the warm water (4), 8.3 kg/h of the water-soluble cationic urea resin (3) ("U-RAMIN P-1500", 40% aqueous solution) and 8.0 kg/h of the anionic surfactant (1% "NEOPELEX" aqueous solution). The preparation of the amino resin prepolymers was repeated except for supplying 19.0 kg/h of the 30%-urea aqueous solution (11) and 13.86 kg/h of the formalin (12) for preparation of urea resin prepolymer, and 30.8 kg/h of the 18%-melamine aqueous dilution (14) and 14.28 kg/h of the formalin (12) for preparation of melamine resin prepolymer. Thereafter, the first and second polycondensation reactions were repeated in the same manner as in Production Example 1 to complete the microencapsulation, thereby obtaining a slurry of microcapsules of Dv=3.9 μm.

Production Example 3

Microencapsulation was performed substantially in a similar manner as in Production Example 1 except for the following modifications.

The first coating step was repeated except for changing the core material (1) to 84.0 kg/h of dichlobenil ("DBN", a herbicide available from Uniroyal, Inc.) and supplying 208.8 kg/h of the warm water (4), 8.6 kg/h of the water-soluble cationic urea resin (3) ("U-RAMIN P-1500", 40% aqueous solution) and 10.0 kg/h of the anionic surfactant (1% "NEOPELEX" aqueous solution). The preparation of the amino resin prepolymers was repeated except for supplying 9.5 kg/h of the 30%-urea aqueous solution (11) and 7.0 kg/h of the formalin (12) for preparation of urea resin prepolymer, and 15.4 kg/h of the 18%-melamine aqueous dilution (14) and 7.1 kg/h of the formalin (12) for preparation of melamine resin prepolymer. Thereafter, the first and second polycondensation reactions were repeated in the same manner as in Production Example 1 to complete the microencapsulation, thereby obtaining a slurry of microcapsules of Dv=6.7 μm.

Production Example 4

Production of Microcapsule (a)

A microcapsule slurry was prepared in the same manner by substantially following the process of GB-A 2113170.

(1) Preparation of Amino Resin Prepolymers 74.1 g of melamine and 238.8 g of formalin (37%-formaldehyde aqueous solution adjusted to pH 8.0 with 20%-triethanolamine aqueous solution) were mixed under stirring together with 338.0 g of water and allowed to react with each other for 30 min. at 50° C. in a reaction vessel to form a melamine resin prepolymer (formaldehyde/melamine=5 (by mol)) liquid.

Separately, 57.0 g of urea and 138.1 g of formalin (37%-aqueous solution adjusted to pH 8.0 with 20%-triethanolamine aqueous solution) were mixed under stirring together with 85.4 g of water and allowed to react each other for 60 min. at 70° C. to form a urea resin prepolymer (formaldehyde/urea=1.8 (by mol)) liquid.

(2) Formation of Microcapsule Slurry

A mixture liquid of 650.9 g of the above-prepared melamine prepolymer liquid, 280.5 g of the above-prepared urea resin prepolymer liquid, 75.5 g of cationic urea resin ("U-RAMIN P-1550", 50% aqueous solution), 110 g of water and 63.0 g of 5%-triethanolamine aqueous solution, was adjusted to pH 4.75 with 10%-citric acid, and then 86.9 g of 1%-aqueous solution of anionic surfactant ("NEOPELEX").

To the liquid system, 750 g of chlorpyrifos (as a core material) was added, and the system was stirred batchwise by means of a high-speed emulsion dispersion stirrer ("TK-HOMOMIXER", available from Tokushu Kika Kogyo K.K.) so as to form an emulsion dispersion liquid containing dispersed liquid droplets in an average particle size of 2-8 μm at 45° C. Thereafter, the system was held at 50° C. under gentle stirring, and 10%-citric acid aqueous solution (as an acid catalyst) was added thereto to adjust the pH to 3.8. After 1 hour, 1066.5 g of water was added, and after further 5 hours, 30%-citric acid aqueous solution (acid catalyst) was added to the system to adjust the pH to 2.8, followed by 18 hours of stirring to complete the microencapsulation, thereby obtaining a slurry of microcapsules of Dv=7.7 μm.

Production Example 5

Production of Microcapsule (b)

To 200 g of chlorpyrifos (core material), 10 g of toluene diisocyanate/trimethylolpropane (1/1 by weight)-adduct was added and stirred together therewith until they formed a uniform mixture. The mixture was added to 400 g of 5%-gum arabic aqueous solution prepared in advance, and the resultant liquid mixture was stirred batchwise by means of a high-speed emulsion dispersion stirrer ("TK-HOMOMIXER") so as to form an emulsion dispersion liquid containing dispersed liquid droplets in an average particle size of 3-10 μm. Thereafter, the system was stirred gently and 10 g of ethylene glycol was added thereto, followed by 24 hours of stirring at 60° C.

to complete the microencapsulation, thereby obtaining a slurry of microcapsules of Dv=5.6 μm.

Example 1

A microcapsule suspension liquid was prepared in the following manner by substantially following a process as represented by a flow chart of FIG. 3.

To 100 wt. parts of the slurry obtained in Production Example 1 and containing 23 wt. parts of chlorpyrifos-microcapsules under stirring, 30%-sodium hydroxide aqueous solution was added to adjust the pH to 6. Separately, in a dispersion vessel, 0.15 wt. part of succinoglycan gum ("RHEOZAN", made by Rhone-Poulene Agrochimie) (thickening agent) was mixed and dispersed together with 3.0 wt. pats of propylene glycol "ADEKA PROPYLENE GLYCOL", available from Asahi Denka K.K.) (water-miscible solvent), and under stirring at 3000-5000 rpm of a high-speed dispersion stirrer ("TK-HOMODISPER", available from Tokushu Kika Kogyo K.K.), pure water was added thereto to form a 1 wt. %-thickening agent aqueous dilution liquid. Then, 15 wt. parts of the 1 wt. %-thickening agent dilution liquid was added to the above-prepared pH-adjusted microcapsule slurry placed in a mixing vessel and under stirring at 50 rpm by means of a paddle stirrer followed by further 2 hours of stirring at 30° C. Thereafter, 0.5 wt. part of sodium polyacrylate ("NEW-KALGEN TG-35", made by Takemoto Yushi K.K.) (dispersing agent) and 0.01 wt. part of silicone oil ("TSA 730", made by Toshiba Silicone K.K.) (anti-forming agent) were added to the system (in the same mixing vessel), and the system was further stirred for 1 hour at 30° C. to obtain a chlorpyrifos-microcapsule suspension liquid (containing ca. 20 wt. % of chlorpyrifos-microcapsule).

Example 2

Ca. 100 wt. parts of a slurry containing 24 wt. parts of chlorpyrifos-microcapsules and adjusted to pH 6 was prepared in a similar manner as in Example 1. Separately, pure water was added to 0.15 wt. part of succinoglycan gum ("RHEOZAN") under stirring at 3000-5000 rpm of a high-speed dispersing stirrer ("TK-HOMODISPER") to prepare 15 wt. parts of 1%-thickening agent aqueous dilution liquid. Further, the 15 wt. parts of 1%-thickening agent aqueous dilution liquid and 30 wt. parts of propylene glycol were added to the above-prepared pH-adjusted microcapsule slurry under stirring at 50 rpm by a paddle stirrer, followed by further 2 hours of stirring at 30° C. Thereafter, 0.5 wt. part of sodium polyacrylate and 0.01 wt. part of silicone oil were added to the system, followed by 1 hour of stirring at 30° C. to obtain a chlorpyrifos-microcapsule suspension liquid.

Example 3

A chlorpyrifos-microcapsule suspension liquid was prepared in the same manner as in Example 2 except for omitting the addition of propylene glycol.

Example 4

A chlorpyrifos-microcapsule suspension liquid was prepared in the same manner as in Example 2 except for directly adding 0.15 wt. part of succinoglycan gum to the pH-adjusted microcapsule slurry instead of the 1%-succinoglycan gum (thickening agent) aqueous dilution liquid.

Example 5

A chlorpyrifos-microcapsule suspension liquid was prepared in the same manner as in Example 2 except for using 30 wt. parts of sodium polyalkylene glycol sulfate ("NEWCOL 240", made by Nippon Nyukazai K.K.) (dispersing agent) instead of the 0.5 wt. part of sodium polyacrylate.

Example 6

A chlorpyrifos-microcapsule suspension liquid was prepared in the same manner as in Example 1 except for replacing the 15 wt. parts of 1%-thickening agent aqueous dilution liquid containing 0.15 wt. part of succinoglycan gum and 3.0 wt. parts of propylene glycol used in Example 1 with 10 wt. parts of 1 wt. %-thickening agent aqueous dilution liquid containing 0.1 wt. part of succinoglycan gum and 3.0 wt. parts of propylene glycol prepared similarly as in Example 1 and 10 wt. parts of thickening agent aqueous dilution liquid containing 5 wt. % of aluminum magnesium silicate ("VEEGUM", made by Vanderbilt Co.).

Example 7

A chlorpyrifos-microcapsule suspension liquid was prepared in the same manner as in Example 1 except for replacing the 15 wt. parts of 1%-thickening agent aqueous dilution liquid containing 0.15 wt. part of succinoglycan gum and 3.0 wt. parts of propylene glycol used in Example 1 with 10 wt. parts of 1 wt. %-thickening agent aqueous dilution liquid containing 0.1 wt. part of succinoglycan gum and 3.0 wt. parts of propylene glycol prepared similarly as in Example 1 and 10 wt. parts of thickening agent aqueous dilution liquid containing 10 wt. % of montmorillonite ("KUNIPIA", made by Kunimine Kogyo K.K.)

Example 8

An ethoprophos-microcapsule suspension liquid was prepared in the same manner as in Example 1 except for adjusting the pH of 100 wt. parts of the slurry containing 23 wt. parts of ethoprophos-microcapsules prepared in Example 2 to 6 similarly as in Example 1, and thereafter adding thereto 12 wt. parts of 1 wt. %-thickening agent aqueous dilution liquid containing 3.0 wt. parts of propylene glycol prepared in a similar manner as in Example 1.

Example 9

A dichlobenil-microcapsule suspension liquid was prepared in the same manner as in Example 1 except for adjusting the pH of 100 wt. parts of the slurry containing 23 wt. parts of dichlobenil-microcapsules prepared in Example 2 to 6 similarly as in Example 1, and thereafter adding thereto 13 wt. parts of 1 wt. %-thickening agent aqueous dilution liquid containing 3.0 wt. parts of propylene glycol prepared in a similar manner as in Example 1.

Example 10

A dichlobenil-microcapsule suspension liquid was prepared in the same manner as in Example 9 except for using 30 wt. parts of sodium polyalkylene glycol sulfate (dispersing agent) instead of the 0.5 wt. part of sodium polyacrylate.

Example 11

A dichlobenil-microcapsule suspension liquid was prepared in the same manner as in Example 9 except for replacing the 0.5 wt. part of sodium polyacrylate with 1.5 wt. parts of polyoxyethylene tristyryl phenyl ether ("SOPROPHOR BSU", made by Rhone-Peulene Agrochimie) and 1.5 wt. parts of polyacrylic acid ("GEROPON DA", made by Rhone-Peulene Agrochimie).

Example 12

100 wt. parts of a slurry containing 21 wt. parts of dichlobenil-microcapsules was adjusted to pH 6 and then, under stirring at 50 rpm by a paddle stirrer, 0.13 wt. part of succinoglycan gum, 3.0 wt. parts of propylene glycol, 0.5 wt. part of sodium polyacrylate and 0.01 wt. part of silicone oil, were directly added thereto to obtain a dichlobenil-microcapsule suspension liquid (containing succinoglycan gum directly added to the aqueous phase similarly as in Example 4).

Example 13

A dichlobenil-microcapsule suspension liquid was prepared in the same manner as in Example 1 except for adjusting the pH of 100 wt. parts of the slurry containing 25.5 wt. parts of dichlobenil-microcapsules prepared in Example 3 to 6 similarly as in Example 1, thereafter dispersing 0.25 wt. part of xanthan gum ("KELZAN S", made by Kelco Division of Merck & Co., Inc.) instead of the 0.15 wt. part of succinoglycan gum in 30 wt. parts of propylene glycol and adding pure water thereto to form 25 wt. parts of 1%-thickening agent aqueous dilution liquid, and then adding the thickening agent aqueous dilution liquid to the above-prepared pH-adjusted microcapsule slurry.

Example 14

A chlorpyrifos-microcapsule suspension liquid was prepared in the same manner as in Example 2 except for using 100 wt. parts of the chlorpyrifos-microcapsule slurry prepared in Production Example 4 instead of the 100 wt. parts of the chlorpyrifos-microcapsule slurry prepared in Production Example 1.

Example 15

A chlorpyrifos-microcapsule suspension liquid was prepared in the same manner as in Example 2 except for using 100 wt. parts of the chlorpyrifos-microcapsule slurry prepared in Production Example 5 instead of the 100 wt. parts of the chlorpyrifos-microcapsule slurry prepared in Production Example 1.

Comparative Example 1

To 100 wt. parts of the slurry containing 21.5 wt. parts of chlorpyrifos-microcapsules prepared in Production Example 1 under stirring at 50 rpm by a paddle stirrer, 30%-sodium hydroxide aqueous solution was added to adjust the pH to 6, and further 0.25 wt. part of xanthan gum ("KELZAN S"), 3.0 wt. parts of propylene glycol and 3.0 wt. parts of sodium polyalkylene glycol sulfate were added thereto, followed further by stirring for 30 min., liquid temperature-raising to 50° C. and stirring for 2 hours, to obtain a chlorpyrifos-microcapsule suspension liquid.

Comparative Example 2

A chlorpyrifos-microcapsule suspension liquid was prepared in the same manner as in Comparative Example 1 except for using 8.0 wt. parts of ammonium polyoxyethylene alkyl ether sulfate ("HI-TENOL", made by Dai-ichi Kogyo Seiyaku K.K.) instead of the 3.0 wt. parts of sodium polyalkylene glycol sulfate.

Comparative Example 3

A chlorpyrifos-microcapsule suspension liquid was prepared in the same manner as in Comparative Example 1 except for using 0.5 wt. part of sodium polyacrylate instead of the 3.0 wt. parts of sodium polyalkylene glycol sulfate.

Comparative Example 4

A chlorpyrifos-microcapsule suspension liquid was prepared in the same manner as in Comparative Example 1 except for using 0.25 wt. part of xanthan gum ("RHODOPOL", available from Rhodia Nikka K.K. (importer to Japan)) instead of 0.25 wt. part of xanthan gum ("KELZAN S").

Comparative Example 5

A chlorpyrifos-microcapsule suspension liquid was prepared in the same manner as in Comparative Example 1 except for using 3.0 wt. parts of montmorillonite ("KUNIPIA F", made by Kunimine Kogyo K.K.) instead of 0.25 wt. part of xanthan gum ("KELZAN S").

Comparative Example 6

A chlorpyrifos-microcapsule suspension liquid was prepared in the same manner as in Comparative Example 1 except for using 0.25 wt. part of rhamsan gum ("KIA-112", available from Sanshosha K.K. (importer to Japan)) instead of 0.25 wt. part of xanthan gum ("KELZAN S").

Comparative Example 7

A chlorpyrifos-microcapsule suspension liquid was prepared in the same manner as in Comparative Example 1 except for using 0.25 wt. part of welan gum ("KIA-96", available from Sanshosha K.K. (importer to Japan)) instead of 0.25 wt. part of xanthan gum ("KELZAN S").

Comparative Example 8

A chlorpyrifos-microcapsule suspension liquid was prepared in the same manner as in Comparative Example 1 except for using 0.25 wt. part of aluminum magnesium silicate ("VEEGUM HV", available from Sanshosha K.K. (importer to Japan)) instead of 0.25 wt. part of xanthan gum ("KELZAN S").

Comparative Example 9

A chlorpyrifos-microcapsule suspension liquid was prepared in the same manner as in Comparative Example 1 except for using 0.25 wt. part of locust bean gum ("GENU GUM RL-200", available from Sanshosha K.K. (importer to Japan)) instead of 0.25 wt. part of xanthan gum ("KELZAN S").

Comparative Example 10

A chlorpyrifos-microcapsule suspension liquid was prepared in the same manner as in Comparative Example 1 except for using 0.25 wt. part of guar gum ("JAGUAR 8111", available from Sanshosha K.K. (importer to Japan)) instead of 0.25 wt. part of xanthan gum ("KELZAN S").

Comparative Example 11

A chlorpyrifos-microcapsule suspension liquid was prepared in the same manner as in Comparative Example 1 except for using 0.25 wt. part of sodium alginate ("KELGIN", available from Sanshosha K.K. (importer to Japan)) instead of 0.25 wt. part of xanthan gum ("KELZAN S").

Comparative Example 12

An ethoprophos-microcapsule suspension liquid was prepared in the same manner as in Comparative Example 1 except for using 100 wt. parts of the ethoprophos-microcapsule slurry prepared in Production Example 2 instead of the 100 wt. parts of chlorpyrifos-microcapsule slurry prepared in Production Example 1.

Comparative Example 13

A dichlobenil-microcapsule suspension liquid was prepared in the same manner as in Comparative Example 1 except for using 100 wt. parts of the dichlobenil-microcapsule slurry prepared in Production Example 3 instead of the 100 wt. parts of chlorpyrifos-microcapsule slurry prepared in Production Example 1.

[Comparative Evaluation Test]

For the purpose of comparison, the following properties were tested with respect to the microcapsule suspension liquids prepared in the above Examples 1-15 and Comparative Examples 1-13.

1. Storage Stability

The stabilization of a microcapsule suspension liquid after storage for a long term under a high temperature sever condition as follows.

For the test, 3 liter of a sample microcapsule suspension liquid was placed in a 3 liter-plugged plastic bottle and left standing at 50° C. for 1 month. The suspension liquid immediately after preparation (initial) and after the storage was subjected to evaluation of appearance and measurement of viscosity and microcapsule particle size in the following manner. The results are inclusively shown in Tables 1 and 2 with respect to Examples and Comparative Examples, respectively.

(1) Average Particle Size (of Microcapsules)

Into a 30 ml-Erlenmeyer flask equipped with a plug, 20 ml of pure water is placed, and a microcapsule suspension liquid sample is added thereto so as to provide a microcapsule content of ca. 2 wt. %. The flask is subjected to 1 min. of vibration at a rate of 120 reciprocations/min. at room temperature. Thereafter, ca. 10 ml of the dispersion liquid sample is injected into a sample path of a laser diffraction-type particle size distribution meter ("Model LA-500", available from Horiba Seisakusho K.K.) to obtain a particle size distribution, from which a volume-average particle size (diameter) (Dv) is calculated.

(2) Viscosity (of Microcapsule Suspension Liquid)

A sample microcapsule suspension liquid in 200 ml is placed in a 200 ml-tall beaker (60 mm dia.×110 mm-H) and left standing under gentle stirring for 1 hour on a thermostat water bath at 30° C. Then, a viscosity measuring rotor ("Brookfield-type", available from Tokyo Keiki K.K.) is pushed into the sample liquid to measure an absolute viscosity.

(3) Appearance

For evaluating the stability of microcapsule suspension liquid, each sample suspension liquid in the 3 liter-plastic bottle after the storage at 50° C. for one month was observed for evaluation of two layer-separation state and measurement of an upper transparent liquid layer thickness. Then, the sample liquid was transferred to a 3 liter-glass beaker separately provided, for further evaluation of the appearance of the sample microcapsule suspension liquid after the storage by observation with eyes. The results are given in Tables 1 and 2 as measured values of the upper transparent layer thickness (UTLT (mm)) and the results of appearance evaluation represented by the following symbols.

A: Uniform viscous suspension liquid with no aggregation of capsule particles.

B1: Uniform viscous suspension liquid with no aggregation but slight caking of capsule particles.

B2: Uniform suspension liquid with slight aggregation and slight caking of capsule particles.

C1: Aggregation and caking of capsule particles.

C2: Aggregation and caking precipitation of capsule particles, and remarkable separation into two layers.

C3: Aggregation and solidified caking precipitation of capsule particles, and remarkable separation into two layers.

C4: Already during the preparation (i.e., mixing of a thickening agent liquid and a microcapsule slurry), aggregation and caking of capsule particles, and remarkable separation into two layers, were observed.

2. Amount of Eluted Core Material in Water

For evaluating the gradual liberation characteristic of a sample microcapsule (rate of liberation of a content material through a microcapsule film), the sample microcapsule is dispersed in water, and the amount of the core material eluted into the water after standing for 24 hours is measured in the following manner.

An amount of sample microcapsule suspension liquid containing 50 mg of an effective component (core material) is sampled into a 200 ml-Erlenmeyer flask equipped with a plug, and 100 ml of pure water is added thereto. After tight plugging, the flask is set in an incubator vibrator and subjected to 2 min. of vibration at a rate of 120 reciprocations/min. on a water bath of 30° C., and then left standing for 24 hours in a thermostat bath of 30° C. A portion of the aqueous phase alone is taken out and sufficiently mixed with acetonitrile added thereto. The mixture liquid is injected into a high-performance liquid chromatograph (HPLC) to measure the content of the core material eluted into water. The results are inclusively shown in Tables 3 and 4 with respect to Examples and Comparative Examples, respectively.

3. Processability (of Microcapsule Suspension Liquid)

The processability (easiness of handling) of a sample microcapsule suspension liquid was evaluated with respect to Foaming of a water-diluted liquid, Suspendability (dispersion characteristic), Re-dispersibility and Clogging (anti-clogging performance) in the following manner. The results are inclusively shown in Tables 3 and 4 with respect to Examples and Comparative Examples, respectively.

(1) Foaming

In a 250 ml-measuring cylinder equipped with a plug, 100 ml of pure water is placed, and an amount of sample microcapsule suspension liquid is added thereto so as to provide a microcapsule content of ca. 2.5 wt. % (ca. 1.0 wt. % after dilution to a total volume of 250 ml, i.e., a microcapsule weight of ca. 2.5 g). Then, pure water is added thereto to make a total volume of 250 ml. After being plugged, the measuring is repetitively turned upside down at a rate of 30 turns per minute for one minute. The height of foaming in the cylinder is measured immediately after and after 1 hour of the turning operation, to give a measure of the foaming characteristic.

(2) Suspendability (Dispersion Characteristic)

A suspension factor as defined below was measured as an index of suspendability in the following manner.

In a 250 ml-measuring cylinder equipped with a plug, 100 ml of pure water is placed, and an amount of sample microcapsule suspension liquid is added thereto so as to provide a microcapsule content of ca. 2.5 wt. % (i.e., ca. 1.0 wt. % after dilution to a total volume of 250 ml). Then, pure water is added thereto up to an uppermost graduation line (making a total volume of 250 ml), to provide a dilution liquid.

After being plugged, the measuring cylinder is turned upside down at a rate of 30 turns per minute for one minute, and then left standing for 1 hour. Then, 25 ml of the dilution liquid is sampled by means of a hole pipet from the central portion of the measuring cylinder. The sampled 25 ml of dilution liquid is placed in a 100 ml-Erlenmeyer flask equipped with a plug, and 0.1 ml of acetic acid and 20 ml of acetone are added thereto. After attaching a cooling tube, the content of the flask is refluxed for 60 min. on a water bath at 50° C. The reflux liquid is cooled, and an internal standard solution (a solution of di-n-propyl phthalate in acetone) is added thereto and fully mixed therewith. The resultant mixture is subjected to gas chromatography to determine an amount of core material in the sample 25 ml-dilution liquid and a ratio thereof to the amount of core material in 25 ml of the dilution liquid in a uniform dispersion state in the cylinder as a suspension factor according to the following formula:

Suspension factor(%)=[weight of core material in the sampled 25 ml of dilution liquid/weight of core material in 25 ml of the dilution liquid in a uniform dispersion state in the cylinder]×100(%).

Incidentally, a suspension factor close to 100% represents a good suspendability, and a microcapsule suspension liquid showing a suspension factor of 85% or higher can be sufficiently used for a practical purpose.

(3) Re-Dispersibility

For measuring a re-dispersibility used herein, a dilution liquid sample is prepared in a 250 ml-measuring cylinder in the same manner as in the Suspendability test (2). Then, the dilution liquid sample is left standing for 24 hours in the measuring cylinder. Thereafter, the measuring cylinder is turned upside down at a rate of 30 turns per minute for one minute to measure the number of turns required for giving a wholly uniform dispersion state of precipitated microcapsules in the cylinder, as a measure of re-dispersibility.

As for a significance of good re-dispersibility, in an ordinary spreading operation of an agricultural chemical, it is rare to use up a once formed dilution liquid, and the remaining dilution liquid is subjected to re-dispersion for use thereof on later days, so that easy re-dispersibility is required. Re-dispersibility in terms of the number of turns required for wholly uniform dispersion of 5 turns or less is judged to be sufficient for re-use after storage of the dilution liquid.

(4) Clogging

A clogging factor is a measure of anti-clogging performance in a spreading or distributing machine, and is measured as a proportion of precipitated microcapsules after standing for 3 hours of a water dilution liquid of a sample microcapsule suspension liquid.

More specifically, for the measurement, 50 liter of pure water is placed in a 100 liter-plastic container, and then an amount of a microcapsule suspension liquid sample sufficient to provide a microcapsule content of ca. 2 wt. % when further diluted to a total volume of 100 liter. The content in the plastic container is gently stirred for 2 minutes by a stirrer having 4 flat paddle blades. Then, pure water is added thereto to make a total volume of 100 liter, and the content is further stirred for 5 minutes for dilution and dispersion, followed by standing. Then, the upper layer dilution liquid is withdrawn out of the container by means of a plastic-made siphon pump (so-called baby pump) gently (e.g., at a withdrawal rate of 3.5-4 kg/min) so as not to suck the precipitated capsules, thereby measuring the weight of the precipitated capsules to calculate a clogging factor according to the following formula:

Clogging factor(%)=[(weight of precipitated capsules)/(weight of capsules added in the dilution liquid)]×100(%).

In an ordinary spreading operation, a larger amount of precipitate in a dilution liquid makes difficult the uniform spreading of microcapsules, i.e., an effective component. A clogging factor of 0.5% or below as calculated above is judged to be sufficient for continuous uniform spreading.

[Mixture Usability Evaluation Test]

Some of the microcapsule suspension liquids obtained in the above Examples and Comparative Examples in an aqueous dilution liquid form were evaluated with respect to the usability thereof in mixture with another agricultural chemical in an undiluted form or in a diluted form. Such a mixture use is frequently adopted in spreading of agricultural chemicals for the purpose of reducing the number of spreading operations and the labor load on spreading operators.

As an outline of the test, 100 ml of pure water is placed in a 250 ml-measuring cylinder equipped with a plug, and an amount of microcapsule suspension liquid sample sufficient to provide a microcapsule of ca. 2.5 wt. % (ca. 1.0 wt. % when further diluted up to 250 ml, i.e., ca. 2.5 g of microcapsules) is added thereto. After plugging, the measuring cylinder is turned upside down at a rate of 30 turns per minute for one minute. Then, another agricultural chemical in an undiluted or diluted form is added in an amount of providing ca. 2.5 wt. % (ca. 1.0 wt. % when diluted to a total amount of 250 ml) of another agricultural chemical, and pure water is further added up to the uppermost graduation line (to make a total volume of 250 ml) to make a dilute mixture liquid. Then, after plugging, the measuring cylinder is further turned upside down at a rate of 30 turns/min. for one minute. The state of the dilution liquid in the measuring cylinder is evaluated by eye observation, and the results thereof are inclusively shown in Table 5 with the following symbols:

A1: The mixture dilution liquid exhibited no aggregation of capsule particles, a uniformly diluted and dispersed state and no damage on the capsules per se; allowed uniform spreading; and therefore exhibited no indication of problem for practical use.

A2: The mixture dilution liquid exhibited slight aggregation of capsule particles, which was at a level of practically no problem at all.

C: Immediately after the addition of another agriculture chemical, the mixture dilution liquid caused aggregation of capsule particles, resulted in a flocky state and caused an immediate sedimentation. The state was judged to be problematic in practical use as to cause spreading irregularity and clogging of the spreading machine.

The contents of the mixture use tests were more specifically as follows.

(Mixture Use Test 1)

12.5 g of the chlorpyrifos-microcapsule suspension liquid (microcapsule content=ca. 20 wt. %) was added to a 250 ml-measuring cylinder already containing 100 ml of pure water and, after the repetitive turning of the cylinder for 1 minute, 2.5 g of DDVP (dichlorobos) (undiluted) (made by Kureha Kagaku Kogyo K.K.) was added thereto, and pure water was further added thereto to make a total volume of 250 ml. After plugging, the cylinder was further turned upside down at a rate of 30 turns/min for 1 min to prepare an aqueous dilution mixture liquid.

(Mixture Use Test 2)

An aqueous dilution mixture liquid was prepared in the same manner as in Mixture use test 1 except for using 5.0 g of DDVP (emulsion) (made by Kureha Kagaku Kogyo K.K.) instead of the 2.5 g of DDVP (undiluted).

(Mixture Use Test 3)

An aqueous dilution mixture liquid was prepared in the same manner as in Mixture use test 1 except for using 12.5 g of chlorpyrifos-microcapsule suspension liquid prepared in Example 2 instead of the 12.5 g of chlorpyrifos-microcapsule suspension liquid prepared in Example 1, and using 5.0 g of DDVP (emulsion) instead of the 2.5 g of DDVP (undiluted).

(Mixture Use Test 4)

An aqueous dilution mixture liquid was prepared in the same manner as in Mixture use test 1 except for using 16.7 g dichlobenil-microcapsule suspension liquid prepared in Example 9 instead of the 12.5 g of chlorpyrifos-microcapsule suspension liquid prepared in Example 1, and using 2.5 g of glyphosate-iso-propylammonium (undiluted) ("ROUNDUP", made by Monsanto Co.) instead of the 2.5 g of DDVP (undiluted).

(Mixture Use Test 5)

An aqueous dilution mixture liquid was prepared in the same manner as in Mixture use test 1 except for using 16.7 g dichlobenil-microcapsule suspension liquid prepared in Example 9 instead of the 12.5 g of chlorpyrifos-microcapsule suspension liquid prepared in Example 1, and using 6.3 g of glyphosate-iso-propylammonium (emulsion) (made by Monsanto Co.) instead of the 2.5 g of DDVP (undiluted).

(Mixture Use Test 6)

An aqueous dilution mixture liquid was prepared in the same manner as in Mixture use test 5 except for using 16.7 g of dichlobenil-microcapsule suspension liquid prepared in Example 10 instead of the 16.7 g of dichlobenil-microcapsule suspension liquid prepared in Example 9.

(Mixture Use Test 7)

An aqueous dilution mixture liquid was prepared in the same manner as in Mixture use test 5 except for using 16.7 g of dichlobenil-microcapsule suspension liquid prepared in Example 11 instead of the 16.7 g of dichlobenil-microcapsule suspension liquid prepared in Example 9.

(Mixture Use Test 8)

An aqueous dilution mixture liquid was prepared in the same manner as in Mixture use test 5 except for using 16.7 g of dichlobenil-microcapsule suspension liquid prepared in Example 12 instead of the 16.7 g of dichlobenil-microcapsule suspension liquid prepared in Example 9.

(Mixture Use Test 9)

An aqueous dilution mixture liquid was prepared in the same manner as in Mixture use test 5 except for using 16.7 g of dichlobenil-microcapsule suspension liquid prepared in Example 13 instead of the 16.7 g of dichlobenil-microcapsule suspension liquid prepared in Example 9.

(Mixture Use Test 10)

An aqueous dilution mixture liquid was prepared in the same manner as in Mixture use test 1 except for using 16.7 g of ethoprophos-microcapsule suspension liquid prepared in Example 8 in addition to the 12.5 g of chlorpyrifos-microcapsule suspension liquid prepared in Example 1.

(Mixture Use Test 11)

An aqueous dilution mixture liquid was prepared in the same manner as in Mixture use test 1 except for using 16.7 g of ethoprophos-microcapsule suspension liquid prepared in Example 15 in addition to the 12.5 g of chlorpyrifos-microcapsule suspension liquid prepared in Example 1.

(Mixture Use Test 12)

An aqueous dilution mixture liquid was prepared in the same manner as in Mixture use test 1 except for using 16.7 g of dichlobenil-microcapsule suspension liquid prepared in Example 9 instead of the 12.5 g of chlorpyrifos-microcapsule suspension liquid prepared in Example 1, and using 5.0 g of DDVP (emulsion) instead of the 2.5 g of DDVP (undiluted).

(Mixture Use Test 13)

An aqueous dilution mixture liquid was prepared in the same manner as in Mixture use test 1 except for using 16.7 g of dichlobenil-microcapsule suspension liquid prepared in Example 9 in addition to the 12.5 g of chlorpyrifos-microcapsule suspension liquid prepared in Example 1.

(Mixture Use Test 14)

An aqueous dilution mixture liquid was prepared in the same manner as in Mixture use test 1 except for using 16.7 g of dichlobenil-microcapsule suspension liquid prepared in Example 9 in addition to the 12.5 g of chlorpyrifos-microcapsule suspension liquid prepared in Example 1, and using 6.3 g of glyphosate-isopropylammonium (emulsion) instead of the 2.5 g of DDVP (undiluted).

(Mixture Use Test 15) (Comparative)

An aqueous dilution mixture liquid was prepared in the same manner as in Mixture use test 1 except for using 12.5 g of chlorpyrifos-microcapsule suspension liquid prepared in Comparative Example 1 instead of the 12.5 g of chlorpyrifos-microcapsule suspension liquid prepared in Example 1.

(Mixture Use Test 16) (Comparative)

An aqueous dilution mixture liquid was prepared in the same manner as in Mixture use test 5 except for using 16.7 g of dichlobenil-microcapsule suspension liquid prepared in Comparative Example 13 instead of the 12.5 g of dichlobenil-microcapsule suspension liquid prepared in Example 9.

The results of the above-mentioned Mixture use tests are inclusively shown in Table 5.

[Activity Test]

Some of the above-prepared aqueous dilution liquids (containing dichlobenil as an active component) were evaluated with respect to their herbicidal activity and residual activity against horsetail (Equisetum) in the following manner.

In the spring, on a horsetail dominant field where horsetail was grown at a height of 30-40 cm, a sample aqueous dilution liquid was uniformly spread at a prescribed rate (600 g of dichlobenil per 10 are) to evaluate its effect of suppressing the growth of horsetail stepwise as follows at an increment of 10% based on coverage with horsetail at 23 days, 44 days and 64 days after the spreading.

| Coverage | Effect |
|---|---|
| 100% | no suppression |
| 90% | suppression by 19% or below |
| 80% | suppression by 20-29% |
| . | . |
| . | . |
| . | . |
| 10% | suppression by 90-99% |
| 0% | completely dead |

The activity test was performed by using mixture dilution liquids obtained in some Mixture use tests and a dilution liquid obtained by diluting the microcapsule suspension liquid of Example 9 to a concentration of 1.0 wt. % of microcapsules.

The results are inclusively shown in Table 6.

TABLE 1

Storage stability test results (Examples)

| | Dv (μm) | | | Viscosity (mPa/s) | | | Appearance after storage | |
|---|---|---|---|---|---|---|---|---|
| Example | Initial (Di) | After storage (Ds) | Ds/Di | Initial (Vi) | After storage (Vs) | Vs/Vi | UTLT (mm) | Appearance |
| 1 | 4.5 | 4.8 | 1.1 | 440 | 470 | 1.1 | 3 | A |
| 2 | 4.6 | 5.5 | 1.2 | 440 | 530 | 1.2 | 4 | A |
| 3 | 4.6 | 5.5 | 1.2 | 440 | 540 | 1.2 | 4 | A |
| 4 | 4.7 | 6.1 | 1.3 | 490 | 690 | 1.4 | 6 | A |
| 5 | 4.5 | 5.2 | 1.2 | 430 | 560 | 1.3 | 5 | A |
| 6 | 4.5 | 5.9 | 1.3 | 460 | 690 | 1.5 | 8 | B1 |
| 7 | 4.5 | 5.2 | 1.2 | 450 | 680 | 1.5 | 8 | B1 |
| 8 | 3.9 | 4.2 | 1.1 | 380 | 410 | 1.1 | 3 | A |
| 9 | 6.1 | 6.9 | 1.1 | 440 | 460 | 1.1 | 3 | A |
| 10 | 6.5 | 8.6 | 1.3 | 380 | 480 | 1.3 | 6 | A |
| 11 | 6.3 | 7.7 | 1.2 | 330 | 420 | 1.3 | 5 | A |
| 12 | 6.5 | 8.5 | 1.3 | 450 | 630 | 1.4 | 7 | A |
| 13 | 6.2 | 9.9 | 1.6 | 460 | 870 | 1.9 | 9 | B2 |

TABLE 1-continued

Storage stability test results (Examples)

| Example | Dv (μm) Initial (Di) | Dv (μm) After storage (Ds) | Ds/Di | Viscosity (mPa/s) Initial (Vi) | Viscosity (mPa/s) After storage (Vs) | Vs/Vi | Appearance after storage UTLT (mm) | Appearance after storage Appearance |
|---|---|---|---|---|---|---|---|---|
| 14 | 7.7 | 9.2 | 1.2 | 460 | 550 | 1.2 | 4 | A |
| 15 | 5.6 | 7.3 | 1.3 | 420 | 550 | 1.3 | 5 | A |

TABLE 2

Storage stability test results (Comparative Examples)

| Comp. Ex | Dv (μm) Initial (Di) | Dv (μm) After storage (Ds) | Ds/Di | Viscosity (mPa/s) Initial (Vi) | Viscosity (mPa/s) After storage (Vs) | Vs/Vi | Appearance after storage UTLT (mm) | Appearance after storage Appearance |
|---|---|---|---|---|---|---|---|---|
| 1 | 5.1 | 17.7 | 3.1 | 610 | 1,530 | 3.3 | 18 | C2 |
| 2 | 4.6 | 9.6 | 2.1 | 490 | 1,860 | 3.8 | 16 | C2 |
| 3 | 4.7 | 11.3 | 2.4 | 480 | 1,440 | 3.0 | 15 | C2 |
| 4 | 8.6 | 26.9 | 3.1 | 400 | >5.000 | >13 | >50 | C3 |
| 5 | 5.3 | 13.3 | 2.5 | 360 | >5.000 | >14 | >50 | C3 |
| 6 | 21.6 | 58.1 | 2.7 | >5.000 | N.M* | | >50 | C4 |
| 7 | 17.7 | 45.5 | 2.6 | >5.000 | N.M* | | >50 | C4 |
| 8 | 4.9 | 14.7 | 3.0 | 80 | 280 | 3.5 | >50 | C2 |
| 9 | 5.3 | 17.6 | 3.3 | 280 | 850 | 3.0 | 40 | C2 |
| 10 | 5.1 | 19.8 | 3.9 | 500 | >5.000 | >10 | >30 | C3 |
| 11 | 5.4 | 15.7 | 2.8 | 110 | 1,760 | 16 | >50 | C2 |
| 12 | 4.2 | 10.3 | 2.5 | 420 | 1,420 | 3.4 | 15 | C1 |
| 13 | 6.8 | 14.8 | 2.2 | 490 | 1,480 | 3.0 | 20 | C1 |

*N.M. = not measurable

TABLE 3

Performances of aqueous dilution liquids (Example)

| Example | Eluted core material in water (ppm) | Foaming (mm) Just after turning | Foaming (mm) After 1 hour | Suspendability (%) | Re-dispersibility (turns) | Clogging factor (%) |
|---|---|---|---|---|---|---|
| 1 | 0.6 | 1~2 | 0 | 93 | 2~3 | 0.1 |
| 2 | 0.6 | 1~2 | 0 | 91 | 3 | 0.2 |
| 3 | 0.6 | 1~2 | 0 | 91 | 3 | 0.2 |
| 4 | 0.7 | 1~2 | 0 | 90 | 3 | 0.3 |
| 5 | 0.6 | 1~2 | 0 | 91 | 4 | 0.2 |
| 6 | 0.6 | 1~2 | 0 | 90 | 4 | 0.3 |
| 7 | 0.6 | 1~2 | 0 | 90 | 4 | 0.3 |
| 8 | 11.0 | 1~2 | 0 | 94 | 2~3 | 0.1 |
| 9 | 4.4 | 1~2 | 0 | 93 | 2~3 | 0.1 |
| 10 | 4.3 | 1~2 | 0 | 91 | 4 | 0.2 |
| 11 | 4.5 | 1~2 | 0 | 92 | 4 | 0.2 |
| 12 | 4.4 | 1~2 | 0 | 92 | 4 | 0.2 |
| 13 | 4.5 | 1~2 | 0 | 90 | 5 | 0.4 |
| 14 | 1.1 | 1~2 | 0 | 91 | 2~3 | 0.2 |
| 15 | 0 | 1~2 | 0 | 94 | 2~3 | 0.1 |

TABLE 4

Performances of aqueous dilution liquids (Comparative Example)

| Comp. Ex | Eluted core material in water (ppm) | Foaming (mm) Just after turning | Foaming (mm) After 1 hour | Suspendability (%) | Re-dispersibility (turns) | Clogging factor (%) |
|---|---|---|---|---|---|---|
| 1 | 0.6 | 40 | 8 | 82 | 6 | 0.7 |
| 2 | 0.7 | 40 | 8 | 78 | 7 | 0.8 |

TABLE 4-continued

Performances of aqueous dilution liquids (Comparative Example)

| Comp. Ex | Eluted core material in water (ppm) | Foaming (mm) | | Suspendability (%) | Re-dispersibility (turns) | Clogging factor (%) |
|---|---|---|---|---|---|---|
| | | Just after turning | After 1 hour | | | |
| 3 | 0.6 | 85 | 70 | 82 | 6 | 0.7 |
| 4 | 0.6 | 60 | 35 | 65 | 15 | 1.1 |
| 5 | 0.7 | 40 | 12 | 30 | 10 | 1.1 |
| 6 | 0.8 | 40 | 10 | 30 | 20 | 1.8 |
| 7 | 0.8 | 40 | 10 | 30 | 20 | 2.0 |
| 8 | 0.6 | 43 | 15 | 30 | 20 | 1.9 |
| 9 | 0.7 | 40 | 10 | 68 | 16 | 0.9 |
| 10 | 0.9 | 40 | 10 | 45 | 19 | 0.9 |
| 11 | 0.8 | 45 | 20 | 30 | 16 | 0.8 |
| 12 | 11.3 | 45 | 12 | 82 | 7 | 0.6 |
| 13 | 4.3 | 45 | 9 | 79 | 9 | 0.9 |

TABLE 5

Mixture use test results (aqueous dilution)

| Test No. | Micro capsule suspension liquid | | Mixed chemical | | Mixture dilution liquid state |
|---|---|---|---|---|---|
| | Example No. | Capsulated chemical | Chemical | Form | |
| 1 | 1 | chlorpyrifos | DDVP | undiluted | A1 |
| 2 | 1 | ↑ | ↑ | emulsion | A1 |
| 3 | 2 | ↑ | ↑ | ↑ | A2 |
| 4 | 9 | dichlobenil | glyphosate | undiluted | A1 |
| 5 | 9 | ↑ | ↑ | emulsion | A1 |
| 6 | 10 | ↑ | ↑ | ↑ | A2 |
| 7 | 11 | ↑ | ↑ | ↑ | A1 |
| 8 | 12 | ↑ | ↑ | ↑ | A1 |
| 9 | 13 | ↑ | ↑ | ↑ | A2 |
| 10 | 1 + 8 | chlorpyrifos ethoprophos | DDVP | undiluted | A1 |
| 11 | 1 + 15 | chlorpyrifos chlorpyrifos | ↑ | ↑ | A1 |
| 12 | 9 | dichlobenil | ↑ | emulsion | A1 |
| 13 | 1 + 9 | chlorpyrifos dichlobenil | ↑ | undiluted | A1 |
| 14 | 1 + 9 | chlorpyrifos dichlobenil | glyphosate | emulsion | A1 |
| 15 | Comp. 1 | chlorpyrifos | DDVP | emulsion | C |
| 16 | Comp. 13 | dichlobenil | glyphosate | emulsion | C |

TABLE 6

Herbicidal effect

| Aqueous dilution liquid | Spreading rate g-dichlobenil/ 10 are | Coverage (%) with hossetail | | |
|---|---|---|---|---|
| | | after 23 days | after 44 days | after 64 days |
| Mixture use test 4 | 600 | 0 | 0 | 10 |
| Mixture use test 5 | 600 | 0 | 0 | 10 |
| Mixture use test 9 | 600 | 0 | 0 | 10 |
| Mixture use test 12 | 600 | 0 | 0 | 10 |
| Mixture use test 13 | 600 | 0 | 0 | 10 |
| Mixture use test 14 | 600 | 0 | 0 | 10 |
| Example 9 (diluted) | 600 | 0 | 0 | 10 |
| None | 0 | 100 | 100 | 100 |

[Evaluation]

As is understood from Tables 1-5, when conventional thickening agents for microcapsule suspension liquid production as represented by xanthan gum (used in Comparative Examples 1-4) were added to a microcapsule slurry in an ordinary manner as in a conventional production process (Comparative Examples 1-13), the resultant microcapsule suspension liquids were liable to cause aggregation or caking after a severe storage test (1 month at 50° C.) corresponding to a long-term storage test, thus being usable, while the difficulty may be alleviated in a short-term storage. However, when xanthan gum as a known microorganism-fermented polysaccharide thickening agent was added to a microcapsule slurry after being diluted with water (Example 13), it provided a microcapsule suspension liquid showing a long-term storage stability durable against the long-term storage test.

On the other hand, succinoglycan gum constantly provided stable microcapsule suspension liquids durable against the severe storage test not only when it was added to a microcapsule slurry after water dilution as a matter of course but also when it was directly added (as in a conventional process) to a microcapsule slurry (Examples 4 and 12). Further, succinoglycan gum exhibited a good suspension stabilization effect also in Mixture use test, and the effect was enhanced particularly when it was added to a microcapsule slurry after dilution with water.

Further, as for the effect of the microcapsule suspension liquid of the present invention, the results in Table 6 show an excellent mixture usability thereof as demonstrated by excellent activities of dichlobenil against the growth of horsetail for dilution liquids of Mixture use tests 4, 5, 9, 12, 13 and 14 (containing other chemicals, i.e., glyphosate (undiluted and emulsion), DDVP (undiluted and emulsion) and chlorpyrifos (capsuled)) which were identical to the activity of the dilution liquid containing only dichlobenil at an identical level formed by diluting the microcapsule suspension liquid of Example 9.

The invention claimed is:

1. A process for producing a microcapsule suspension liquid, comprising:

(I) a step of mixing a thickening agent comprising a microorganism-fermented succinoglycan polysaccharide and propylene glycol for dilution with water to form a dilute thickening agent aqueous solution, (II) a step of dispersing microcapsules comprising a core material and a resinous coating in an aqueous medium to form a microcapsule slurry, and (III) a step of mixing the above-formed microcapsule suspension liquid with the above-formed dilute thickening agent aqueous solution, followed by addition thereto of sodium polyacrylate and an anti-foaming agent comprising silicone, wherein the microcapsules have a resinous coating layer comprising a successive laminate including a solidified layer of coacervate of a water-soluble cationic amino resin and an anionic surfactant and a layer of polycondensate of amino resin prepolymer, obtained through a process comprising a step of mixing the core material and an anionic surfactant aqueous solution and then with a pH-adjusted aqueous solution of the water-soluble cationic amino resin to coat the core material with the coacervate of the water-soluble cationic amino resin and the anionic surfactant, a step of mixing the coacervate-coated core material with an amino resin prepolymer liquid, and a step of adding an acidic catalyst to polycondense the amino resin prepolymer, and in the step (I), the thickening agent is first mixed and dispersed together with the propylene glycol, and then is diluted with water to form the dilute thickening agent aqueous solution.

* * * * *